United States Patent
Kumaki et al.

(10) Patent No.: US 11,389,115 B2
(45) Date of Patent: Jul. 19, 2022

(54) PIEZOELECTRIC SENSOR

(71) Applicant: NATIONAL UNIV CORP YAMAGATA UNIVERSITY, Yamagata (JP)

(72) Inventors: Daisuke Kumaki, Yamagata (JP); Junichi Toukairin, Yamagata (JP); Shizuo Tokito, Yamagata (JP)

(73) Assignee: NATIONAL UNIVERSITY CORPORATION YAMAGATA UNIVERSITY, Yamagata (JP)

(*) Notice: Subject to any disclaimer, the term of this patent is extended or adjusted under 35 U.S.C. 154(b) by 0 days.

(21) Appl. No.: 17/269,575

(22) PCT Filed: Mar. 27, 2020

(86) PCT No.: PCT/JP2020/014016
§ 371 (c)(1),
(2) Date: Feb. 19, 2021

(87) PCT Pub. No.: WO2020/203771
PCT Pub. Date: Oct. 8, 2020

(65) Prior Publication Data
US 2022/0039748 A1    Feb. 10, 2022

(30) Foreign Application Priority Data
Mar. 29, 2019  (JP) .............................. JP2019-068025

(51) Int. Cl.
*H01L 41/047* (2006.01)
*H01L 41/113* (2006.01)
(Continued)

(52) U.S. Cl.
CPC .......... *A61B 5/6843* (2013.01); *H01L 41/047* (2013.01); *H01L 41/1132* (2013.01); *A61B 2562/0247* (2013.01); *H01L 41/193* (2013.01)

(58) Field of Classification Search
CPC .......................... H01L 41/1132; H01L 41/047
(Continued)

(56) References Cited

U.S. PATENT DOCUMENTS 9,127,996 B2    9/2015  Kawai et al.
9,627,605 B2    4/2017  Ando et al.
(Continued)

FOREIGN PATENT DOCUMENTS

CN    102047088 A    5/2011
CN    103308221 A    9/2013
(Continued)

OTHER PUBLICATIONS

International Search Report cited in International Appln. PCT/JP2020/014016 dated May 28, 2020.
(Continued)

*Primary Examiner* — Derek J Rosenau
(74) *Attorney, Agent, or Firm* — Bacon & Thomas, PLLC

(57) ABSTRACT

A piezoelectric sensor configured to detect a change of pressure from a living body in a predetermined location includes: a pair of electrodes spaced from one another and formed to spread as a sheet; a pressure-sensitive layer disposed between the pair of electrodes and configured to generate electric charge in response to the change of pressure; a pair of terminals connected to the pair of electrodes, respectively, and configured to output an electrical signal supplied from the pair of electrodes in response to the change of pressure of the living body. An edge of at least one of the pair of electrodes extending toward the pair of terminals is disposed to protrude outside the pressure-sensitive layer, and the electrical signal propagates through the edge and is outputted from the pair of terminals.

4 Claims, 3 Drawing Sheets

(51) Int. Cl.
*H01L 41/193* (2006.01)
*A61B 5/00* (2006.01)

(58) Field of Classification Search
USPC .......................................... 310/338, 365, 366
See application file for complete search history.

(56) References Cited

U.S. PATENT DOCUMENTS

| | | | |
|---|---|---|---|
| 2009/0289529 | A1 | 11/2009 | Ito et al. |
| 2009/0293631 | A1 | 12/2009 | Radivojevic |
| 2012/0055257 | A1* | 3/2012 | Shaw-Klein ........ H01L 41/1132 73/780 |
| 2012/0144925 | A1 | 6/2012 | Radivojevic |
| 2013/0233089 | A1 | 9/2013 | Kawai et al. |
| 2018/0161814 | A1* | 6/2018 | Buckland ................ G01F 1/667 |
| 2019/0386198 | A1 | 12/2019 | Ando et al. |

FOREIGN PATENT DOCUMENTS

| | | |
|---|---|---|
| CN | 103492832 A | 1/2014 |
| JP | 5831542 B2 | 11/2015 |
| JP | 5895615 | 3/2016 |
| JP | 2018-33497 A | 3/2018 |
| WO | WO2016027615 A1 | 2/2016 |

OTHER PUBLICATIONS

Extended European Search Report (EESR) dated Nov. 5, 2021 in corresponding European Patent Appln. No. 20782582.9.
Chinese First Office Action dated Dec. 24, 2021 in corresponding Chinese Patent Appln. No. 202080004680.8.

* cited by examiner

PIEZOELECTRIC SENSOR

TECHNICAL FIELD

The present invention relates to a piezoelectric sensor, more specifically, to a piezoelectric sensor configured to detect a change of pressure from a living body due to heartbeat and breathing in a predetermined location.

BACKGROUND ART

Conventionally, piezoelectric sensors configured to detect a change of pressure from a living body due to heartbeat and breathing have been in practical use. For example, by disposing a piezoelectric sensor on a bed in a hospital, it is possible to continuously detect changes of pressure from a living body to easily know the condition of the living body.

As this piezoelectric sensor, for example, there has been proposed one which is provided with a plurality of piezoelectric elements. With the plurality of piezoelectric elements provided in the piezoelectric sensor, it is possible to detect changes of pressure of parts of the living body, and therefore to precisely know the condition of the living body. However, there have been problems with the complexity of the device configuration because, for example, an electric signal from each of the piezoelectric elements is analyzed by using an individual arithmetic circuit.

Therefore, as a technology for simplifying the configuration, there has been proposed a piezoelectric sensor structure configured to be able to accurately measure biological signals in any locations in, for example, Patent Literature 1. This piezoelectric sensor structure includes electrodes formed to spread as a sheet in the width direction of the bed, and therefore it is possible to detect a change of pressure in a large area by a simple configuration.

CITATION LIST

Patent Literature

PTL 1: Japanese Patent Application Laid-Open No. 2018-33497

SUMMARY OF INVENTION

Technical Problem

However, in the piezoelectric sensor structure disclosed in Patent Literature 1, a pressure-sensitive layer is disposed to cover the whole area of the electrodes, and therefore, for example, capacitive coupling may occur between the pressure-sensitive layer and the electrodes until an electric signal generated in response to a change of pressure propagates through the electrodes and reaches the terminals, and consequently the signal waveform may be changed.

To solve this conventional problem, it is therefore an object of the invention to provide a piezoelectric sensor configured to prevent the effect of the pressure-sensitive layer on the electrical signals propagating through the electrodes.

Solution to Problem

According to an aspect of the invention, a piezoelectric sensor configured to detect a change of pressure from a living body in a predetermined location includes: a pair of electrodes spaced from one another and formed to spread as a sheet; a pressure-sensitive layer disposed between the pair of electrodes and configured to generate electric charge in response to the change of pressure; a pair of terminals connected to the pair of electrodes, respectively, and configured to output an electrical signal supplied from the pair of electrodes in response to the change of pressure of the living body. An edge of at least one of the pair of electrodes extending toward the pair of terminals is disposed to protrude outside the pressure-sensitive layer, and the electrical signal propagates through the edge and is outputted from the pair of terminals.

It is preferred that an edge of each of the pair of electrodes is disposed to protrude outside the pressure-sensitive layer.

It is preferred that an entire circumference of the edge of at least one of the pair of electrodes is disposed to protrude outside the pressure-sensitive layer.

It is preferred that each of the pair of electrodes has a long rectangular shape, and at least one of the pair of electrodes includes a plurality of detecting parts divided from each other by slits which extends over a part overlapping the pressure-sensitive layer in a direction crossing a longitudinal direction.

The plurality of detecting parts may be further divided by a silt extending in the longitudinal direction.

The pair of electrodes may be connected to edges of the pair of electrodes extending in a lateral direction.

Advantageous Effect

According to the invention, the edge of at least one of the pair of electrodes which extends to the pair of terminals is disposed to protrude outside the pressure-sensitive layer, and therefore the electric signals propagate through the edge and are outputted from the pair of terminals. By this means, it is possible to provide a piezoelectric sensor configured to prevent the effect of the pressure-sensitive layer on the electric signals propagating through the electrodes.

DESCRIPTION OF EMBODIMENTS

Hereinafter, the embodiments of the invention will be described with reference to the accompanying drawings.

Embodiment 1

Figure 1A:
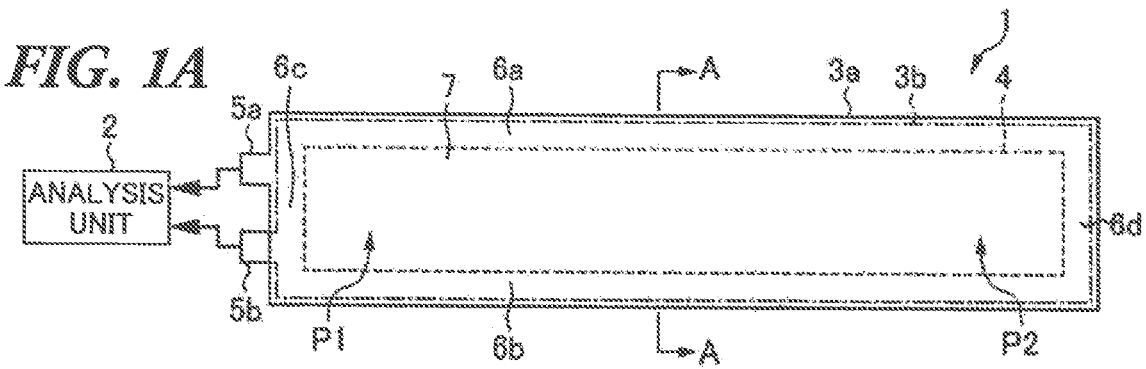
FIG. 1A is a plan view illustrating the configuration of a biological information analyzer including a piezoelectric sensor according to Embodiment 1 of the invention.
Figure 1B:
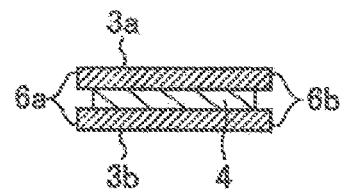
FIG. 1B is a cross-sectional view taken along line A-A of FIG. 1A.

FIGS. 1A and 1B illustrate the configuration of a biological information analyzer including a piezoelectric sensor according to Embodiment 1 of the invention. This biological information analyzer includes a piezoelectric sensor 1 and an analysis unit 2.

The piezoelectric sensor 1 is configured to detect a change of pressure from a living body in a predetermined location, and includes a pair of electrodes 3a and 3b, a pressure-sensitive layer 4, and a pair of terminals 5a and 5b. Here, the change of pressure includes a minor change of pressure such as a vibration on the surface of a living body, as well as a major change of pressure applied from the whole living body. The electrodes 3a and 3b are spaced from one another, and each of them has the same long rectangular shape. The electrodes 3a and 3b may be formed of, for example, a conductive material such as a metallic material and an organic conductive material.

The pressure-sensitive layer 4 is configured to generate electric charge in response to a change of pressure, and disposed between the electrodes 3a and 3b. The pressure-sensitive layer 4 may be formed of, for example, a ferroelectric material, such as a polyvinylidene fluoride (PVDF), and a poly(vinylidene-trifluoroethylene) copolymer (P(VDF-TrFE)). Alternatively, the pressure-sensitive layer 4 may be formed of a polymeric material such as polylactic acid and polyurea, and an electret material obtained by charging a porous film.

Here, the area of the pressure-sensitive layer 4 is smaller than that of the electrodes 3a and 3b. To be more specific, two edges 6a and 6b of each of the electrodes 3a and 3b which extend in the longitudinal direction, and two edges 6c and 6d of each of the electrodes 3a and 3b which extend in the lateral direction protrude outside the pressure-sensitive layer 4. That is, the entire circumference of the edges 6a to 6d of each of the electrodes 3a and 3b protrudes outside the pressure-sensitive layer 4. By this means, a detecting part 7 electrically connected to the pressure-sensitive layer 4 is disposed in part of the electrodes 3a and 3b overlapping the pressure-sensitive layer 4 in the direction in which the electrodes 3a and 3b are stacked, and the edges 6a to 6d are disposed around the detecting part 7 without overlapping the pressure-sensitive layer 4. Here, it is preferred that the detecting part 7 is formed to spread as a sheet and has the widest portion equal to or greater than 10 cm.

The terminals 5a and 5b are connected to the electrodes 3a and 3b, respectively, and sequentially output electrical signals supplied from the electrodes 3a and 3b in response to a change of pressure from a living body. The analysis unit 2 is configured to analyze biological information of the living body, based on the electrical signals outputted from the terminals 5a and 5b. The analysis unit 2 can calculate the biological information such as a heart rate, a respiration rate, and a body movement based on, for example, a frequency of electrical signals.

Figure 2:
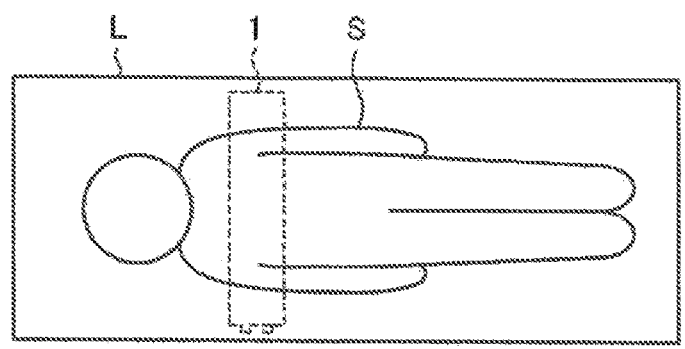
FIG. 2 illustrates a state where the piezoelectric sensor is disposed on a bed.

Next, the operation of Embodiment 1 will be described. First, as illustrated in FIG. 2, the piezoelectric sensor 1 is disposed in a predetermined location to allow a living body S to lie down, such as a bed L. The piezoelectric sensor 1 has a long rectangular shape to extend in the width direction of the bed L, and therefore can precisely detect a change of pressure from the living body S.

As illustrated in FIGS. 1A and 1B, when the change of pressure from the living body S is applied to the piezoelectric sensor 1, an electrical signal corresponding to the change of pressure from the living body S is supplied from the detecting part 7. This electrical signal will propagate through the electrodes 3a and 3b to the terminals 5a and 5b from the pressed position to which the change of pressure from the living body S is applied. Here, the strength of the electrical signal having propagated through the detecting part 7 in the electrodes 3a and 3b may significantly attenuate due to the effect of capacitive coupling between the detecting part 7 and the pressure-sensitive layer 4. In particular, when the detecting part 7 is pressed at the pressed position P2 far from the terminals 5a and 5b, the electrical signal is more affected by the capacitive coupling between the detecting part 7 and the pressure-sensitive layer 4 than when the pressed position P1 close to the terminals 5a and 5b is pressed, because the propagation distance of the electrical signal is longer.

Therefore, each of the electrodes 3a and 3b includes the edges 6a to 6d extending from the pressed position P2 to the terminals 5a and 5b. These edges 6a to 6d are disposed to protrude outside the pressure-sensitive layer 4, that is, disposed not to overlap the pressure-sensitive layer 4 in the stacking direction. Therefore, the electrical signal propagating through the edges 6a to 6d can reach the terminals 5a and 5b without the effect of the capacitive coupling between the detecting part 7 and the pressure-sensitive layer 4. In particular, it is possible to prevent the electrical signal generated at the pressed position P2 far from the terminals 5a and 5b from attenuating due to the effect of the capacitive coupling, and therefore to output all of the electrical signals with a certain level of strength from the terminals 5a and 5b to the analysis unit 2 regardless of the distance from the terminals 5a and 5b.

Here, the entire circumference of the edges 6a to 6d of each of the electrodes 3a and 3b is disposed to protrude outside the pressure-sensitive layer 4, and therefore it is possible to surely propagate the electrical signals via the edges 6a to 6d, when either the pressed positions P1 or P2 is pressed. Here, each of the edges 6a to 6d may have a width of, for example, about 1 cm.

In this way, the electrical signals outputted from the terminals 5a to 5b to the analysis unit 2 include the electrical signals having propagated through the edges 6a to 6d, and therefore maintain their strength. Therefore, the analysis unit 2 can calculate the biological information of the living body S, based on the electrical signals with the maintained strength, and therefore highly precisely calculate the biological information. In particular, an electrical signal caused by a heartbeat has a relatively high frequency of, for example, 1 Hz to 10 Hz, and therefore tends to attenuate. However, by preventing the attenuation of the electrical signal, it is possible to precisely calculate the biological information having a relatively high frequency.

With the present embodiment, the edges 6a to 6b of each of the electrodes 3a and 3b extending toward the terminals 5a and 5b are disposed to protrude outside the pressure-sensitive layer 4, and therefore the electrical signals propagate through the edges 6a to 6d and are outputted from the terminals 5a and 5b. By this means, it is possible to prevent the effect of the pressure-sensitive layer 4 on the electrical signals propagating through the electrodes 3a and 3b.

Embodiment 2

With the above-described Embodiment 1, the entire circumference of the edges 6a to 6d of each of the electrodes 3a and 3b is disposed to protrude outside the pressure-sensitive layer 4. However, this is by no means limiting as long as the edges extending toward the terminals 5a and 5b are disposed to protrude outside the pressure-sensitive layer 4.

Figure 3A:
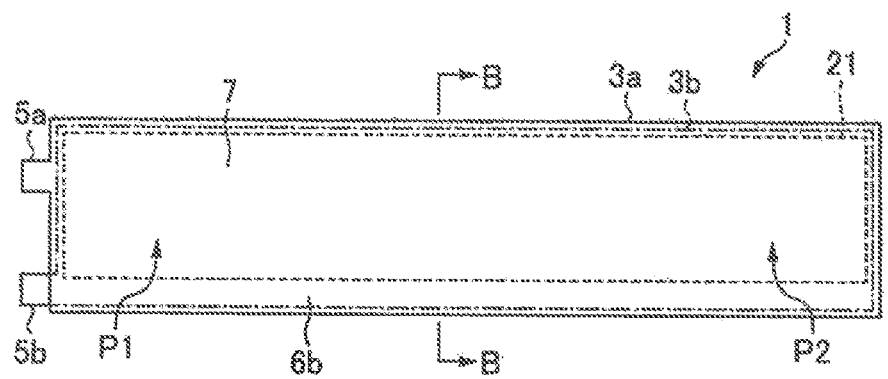
FIG. 3A is a plan view illustrating the configuration of a piezoelectric sensor according to Embodiment 2 of the invention.
Figure 3B:
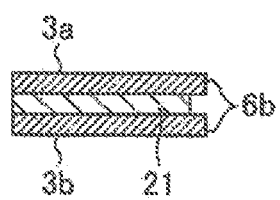
FIG. 3B is a cross-sectional view taken along line B-B of FIG. 3A.

For example, as illustrated in FIGS. 3A and 3B, a pressure-sensitive layer 21 may be disposed, instead of the pressure-sensitive layer 4 according to Embodiment 1. This pressure-sensitive layer 21 has an area smaller than that of each of the electrodes 3a and 3b by the edge 6b. That is, only the edge 6b of each of the electrodes 3a and 3b extending toward the terminals 5a and 5b is disposed to protrude outside the pressure-sensitive layer 21. Here, it is preferred that the terminal 5b is disposed on an extension of the edge 6b and connected directly to the edge 6b. Alternatively, the terminal 5a may be disposed on an extension of the edge 6b and connected directly to the edge 6b.

With this configuration, even when the detecting part 7 is pressed at the pressed position P2 far from the terminals 5a and 5b, it is possible to prevent the electrical signals propagating through the edge 6b from attenuating due to the effect of the capacitive coupling between the detecting part 7 and the pressure-sensitive layer 21. Consequently, it is possible to output the electrical signals with the maintained strength from the terminals 5a and 5b.

According to the present embodiment, the edge 6b of each of the electrodes 3a and 3b extending toward the terminals 5a and 5b is disposed to protrude outside the pressure sensitive layer 21, and the electrical signals propagate through the edge 6b and are outputted from the terminals 5a and 5b. Therefore, it is possible to prevent the effect of the pressure-sensitive layer 21 on the electrical signals propagating through the electrodes 3a and 3b.

Embodiment 3

With the above-described Embodiments 1 and 2, the edges of the electrodes 3a and 3b, which face each other, are disposed to protrude outside the pressure-sensitive layer. However, this is by no means limiting as long as the edges extending toward the terminals 5a and 5b are disposed to protrude outside the pressure-sensitive layer.

Figure 4A:
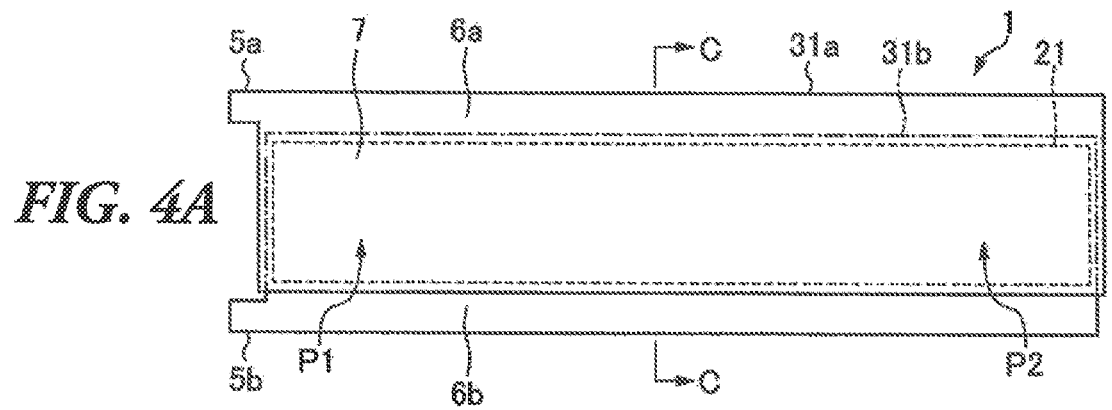
FIG. 4A is a plan view illustrating the configuration of a piezoelectric sensor according to Embodiment 3 of the invention.
Figure 4B:
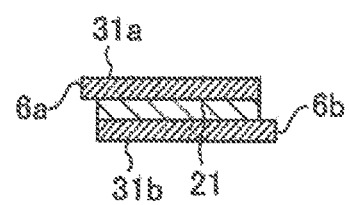
FIG. 4B is a cross-sectional view taken along line C-C of FIG. 4A.

For example, as illustrated in FIGS. 4A and 4B, electrodes 31a and 31b may be disposed, instead of the electrodes 3a and 3b according to Embodiment 2. Here, the edge 6a of the electrode 31a extending toward the terminals 5a and 5b is disposed to protrude outside the pressure-sensitive layer 21. Meanwhile, the edge 6b of the electrode 31b extending toward the terminals 5a and 5b is disposed to protrude outside the pressure-sensitive layer 21. That is, the edges 6a and 6b of the electrodes 3a and 3b facing the opposite sides one another are disposed to protrude outside the pressure-sensitive layer 21. Here, it is preferred that the terminal 5a is disposed on an extension of the edge 6a and connected directly to the edge 6a, and that the terminal 5b is disposed on an extension of the edge 6b and connected directly to the edge 6b.

With this configuration, even when the detecting part 7 is pressed at the pressed position P2 far from the terminals 5a and 5b, it is possible to prevent the electrical signals propagating through the edges 6a and 6b from attenuating due to the effect of the capacitive coupling between the detecting part 7 and the pressure-sensitive layer 21. Therefore, it is possible to output the electrical signals with the maintained strength from the terminals 5a and 5b. In addition, the edges 6a and 6b of the electrodes 3a and 3b, which face the opposite sides one another, are disposed to protrude outside the pressure-sensitive layer 21, and therefore it is possible to prevent a short circuit due to direct contact between the edges 6a and 6b.

According to the present embodiment, the edges 6a and 6b of the electrodes 31a and 31b, which face the opposite sides one another, are disposed to protrude outside the pressure-sensitive layer 21, and therefore it is possible to prevent an electrical short, circuit due to contact between the edges 6a and 6b.

Embodiment 4

With the above-described Embodiments 1 to 3, one detecting part 7 is disposed in part of the electrodes 3a and 3b overlapping the pressure-sensitive layer 4 in the stacking direction. However, this is by no means limiting as long as it is possible to detect a change of pressure from the living body S, and a plurality of detecting parts 7 may be disposed. To be more specific, the electrodes 3a and 3b may include a plurality of detecting parts divided from each other by slits which extend over the part overlapping the pressure-sensitive layer 4 in the direction crossing the longitudinal direction.

Figure 5:
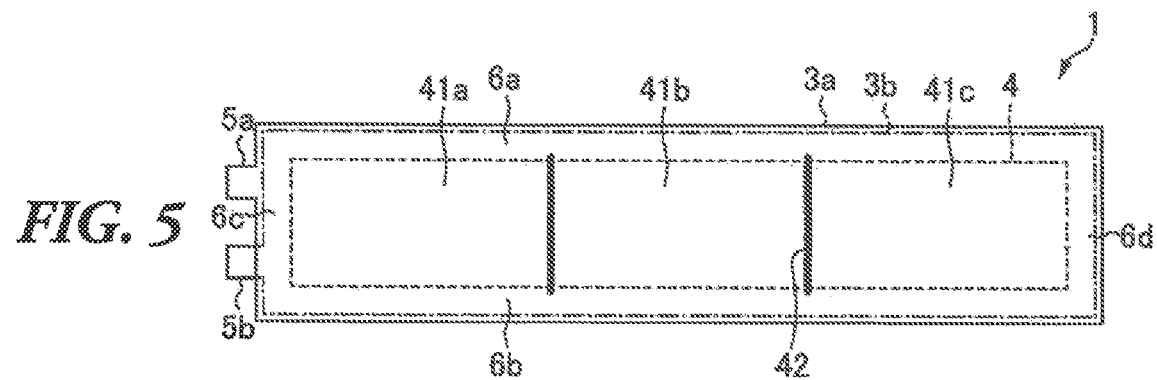
FIG. 5 illustrates the configuration of a piezoelectric sensor according to Embodiment 4.

For example, as illustrated in FIG. 5, detecting parts 41a, 41b, and 41c may be disposed, instead of the detecting part 7 in the electrodes 3a and 3b according to Embodiment 1. These detecting parts 41a and 41c are divided from each other by two slits 42 which extend over the part of the electrodes 31 and 3b overlapping the pressure-sensitive layer 4 in the direction orthogonal to the longitudinal direction of the electrodes 3a and 3b. Here, the slits 42 dividing the detecting parts 41a to 41c are formed to extend longer than the width of the pressure-sensitive layer 4 to entirely go across the pressure-sensitive layer 4.

With this configuration, the electrical signals supplied from the detecting parts 41a to 41c in response to a change of pressure from the living body S are blocked by the slits 42 and therefore cannot propagate through the detecting parts 41a to 41c, but propagate through the edges 6a to 6d and reach the terminals 5a and 5b. In this way, the electrical signals propagate through the edges 6a to 6d and reach the terminals 5a and 5b, and therefore it is possible to surely prevent the strength from attenuating due to the capacitive coupling between the detecting parts and the pressure-sensitive layer 4.

According to the present embodiment, the detecting parts 41a to 41c of the electrodes 3a and 3b are divided from each other by the slits 42, and therefore it is possible to propagate the electrical signals from the detecting part 41a to 41c to the terminals 5a and 5b via the edges 6a to 6d. Consequently, it is possible to surely prevent the effect of the pressure-sensitive layer 4 on the electrical signals.

Embodiment 5

With the above-described Embodiment 4, the electrodes 3a and 3b includes the detecting parts 41a to 41c divided from each other by the slits 42 which extend over the part overlapping the pressure-sensitive layer 4 in the direction crossing the longitudinal direction. However, this is by no means limiting, but the plurality of detecting parts may be divided from each other by a silt extending in the longitudinal direction.

Figure 6:
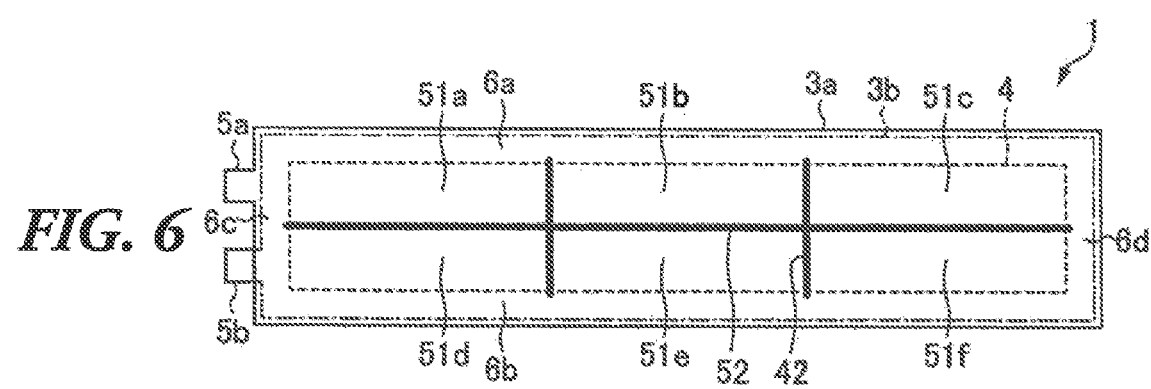
FIG. 6 illustrates the configuration of a piezoelectric sensor according to Embodiment 5.

For example, as illustrated in FIG. 6, the electrodes 3a and 3b according to Embodiment 4 may include detecting parts 51a, 51b, 51c, 51d, 51e, and 51f, instead of the detecting parts 41a to 41c. These detecting parts 5la to 51f are divided from each other by the slits 42 in the longitudinal direction in the same way as Embodiment 4, and also divided from each other by a slit 52 which extends over the part overlapping the pressure-sensitive layer 4 in the longitudinal direction. Here, the slit 52 dividing the detecting parts 51a to 51f is formed to extend longer than the length of the pressure-sensitive layer 4 in the longitudinal direction, and therefore to entirely go across the pressure-sensitive layer 4. Likewise, the slits 42 are formed to extend longer than the width of the pressure-sensitive layer 4 in the lateral direction, and therefore to entirely go across the pressure-sensitive layer 4.

With this configuration, the electrical signals supplied from the detecting parts 51a to 51f in response to a change of pressure from the living body S are blocked by the slits 42 and 52, and therefore cannot propagate through the detecting parts 51a to 51f, but propagate through the edges 6a to 6d and reach the terminals 5a and 5b. In this case, the slit 52 is formed to extend in the longitudinal direction, and therefore the electrical signals supplied from the detecting parts 51a to 51c are propagated via the edge 6a, and the electrical signals supplied from the detecting parts 51d to 51f are propagated via the edge 6b. That is, it is possible to propagate the electrical signals via the edges 6a to 6d which are closest to the detecting parts 51a to 51f, and therefore to more surely prevent the electrical signals from attenuating due to the effect of the capacitive coupling between the detecting parts and the pressure-sensitive layer 4.

According to the present embodiment, the detecting parts 51a to 51f of the electrodes 3a and 3b are divided from each other by the slits 42 and 52. By this means, it is possible to propagate the electrical signals via the edges 6a to 6d which are closest to the detecting parts 51a to 51f, and therefore to more surely prevent the effect of the pressure-sensitive layer 4 on the electrical signals.

Here, with the above-described Embodiments 1 to 5, the edges of the electrodes 3a and 3b are disposed to protrude outside the pressure-sensitive layer 4, respectively. However, this is by no means limiting as long as the edge of at least one of the electrodes 3a and 3b is disposed to protrude outside the pressure-sensitive layer 4. For example, when the terminal 5a of the electrode 3a is connected to the analysis unit 2, and the terminal 5b of the electrode 3b is grounded, the edge of only the electrode 3a may be disposed to protrude outside the pressure-sensitive layer 4, and the whole area of the electrode 3b may be disposed to face the pressure-sensitive layer 4.

In addition, with the above-described Embodiments 1 to 5, each of the electrodes 3a and 3b has a long rectangular shape. However, this is by no means limiting as long as each of the electrodes 3a and 3b is formed to spread as a sheet. Moreover, with the above-described Embodiments 1 to 5, each of the electrodes 3a and 3b is formed to spread in two dimensions, but this is by no means limiting. Each of the electrodes 3a and 3b may be curved in three dimensions.

Furthermore, with the above-described Embodiments 1 to 5, the piezoelectric sensor 1 is used for bedding disposed on the bed L. However, this is by no means limiting as long as it is possible to detect a change of pressure from the living body S in a predetermined location. For example, the piezoelectric sensor 1 may be used for a seat on which the living body S sits.

EXAMPLES

Next, examples will be illustrated to specifically describe the invention.

Example 1

The electrodes 3a and 3b were produced by cutting a copper foil film with a conductive adhesive layer into two sheets each having a width of 8.5 cm and a length of 61 cm. The pressure-sensitive layer 4 was produced by cutting a PVDF film (KUREHA KF POLYMER produced by KUREHA) into a sheet having a width of 6.5 cm and a length of 60 cm. The pressure-sensitive layer 4 was stuck on the electrode 3b, and then the electrode 3a was stuck on the pressure-sensitive layer 4. Here, the three edges 6a, 6b and 6c of each of the electrodes 3a and 3b were disposed to protrude outside the pressure-sensitive layer 4 by 1 cm. Therefore, the detecting part 7 was formed in size with a width of 6.5 cm and a length of 60 cm. By this means, a piezoelectric sensor was produced.

Comparative Example 1

A pair of electrodes was produced by cutting a copper foil film with a conductive adhesive layer into two sheets each having a width of 6.5 cm and a length of 60 cm. A pressure-sensitive layer was produced by cutting a PVDF film (KUREHA KF POLYMER produced by KUREHA) into a sheet having a width of 8.5 cm and a length of 61 cm. The pressure-sensitive layer was stuck on one of the electrodes, and then the other electrode was stuck on the pressure-sensitive layer. Here, the pair of electrodes was disposed such that the whole area faced the pressure-sensitive layer, and a detecting part was formed in size with a width of 6.5 cm and a length of 60 cm. By this means, a piezoelectric sensor was produced.

<Evaluation Method>

An oscilloscope was connected to the produced piezoelectric sensor via an amplifier, and the strength of an electrical signal was measured when the piezoelectric sensor previously pressed at 10 N by a shaker was pressed at 17.5 N. The pressing by the shaker was achieved by applying vibrations to a pressed position P1 close to the connection point to the oscilloscope and a pressed position P2 far from the connection point at different frequencies of 0.25 Hz to 10 Hz, respectively. The results are illustrated in FIGS. 7 and 8.

Figure 7:
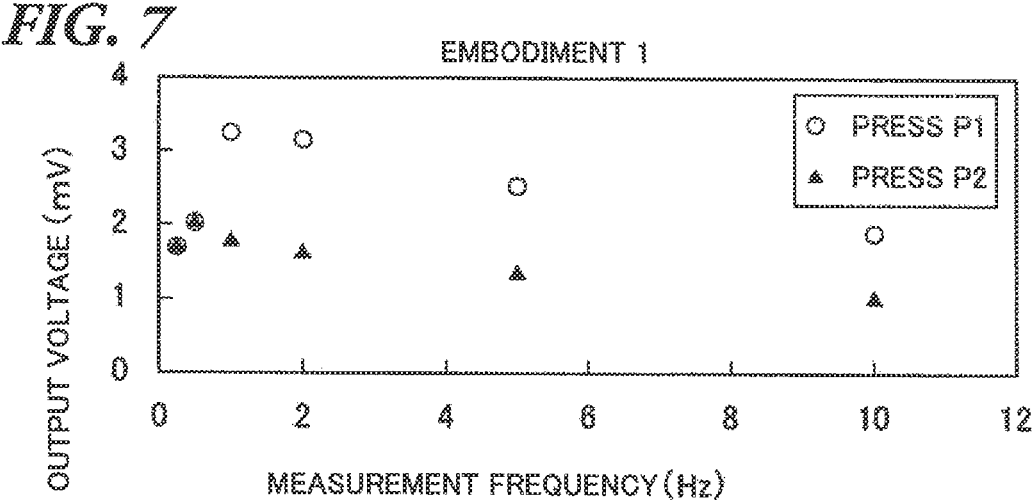
FIG. 7 is a graph illustrating changes in the strength of electric signals when the piezoelectric sensor according to Embodiment 1 is pressed.
Figure 8:
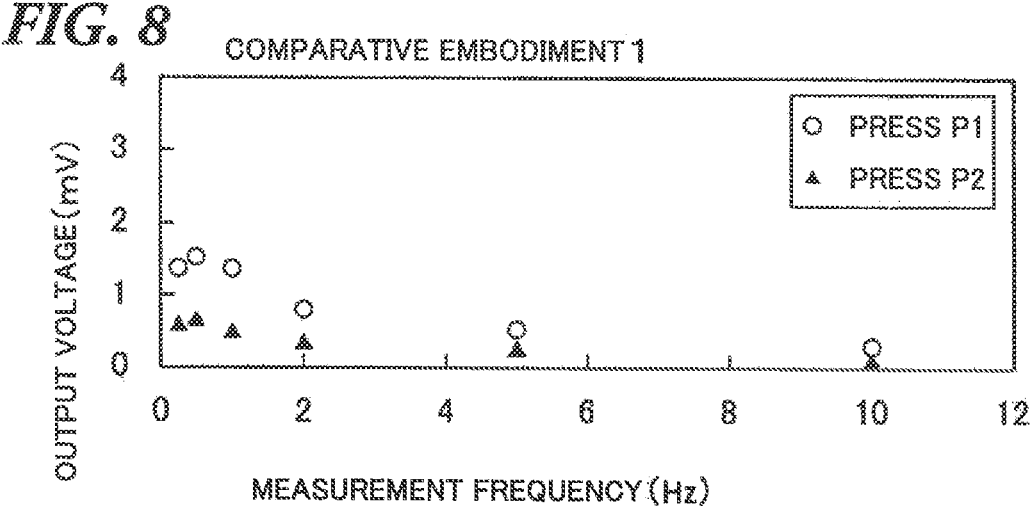
FIG. 8 is a graph illustrating changes in the strength of electric signals when the piezoelectric sensor according to Comparative embodiment 1 is pressed.

From the measurement results illustrated in FIGS. 7 and 8, it is found that the strength of the electrical signals with Embodiment 1 where the three edges 6a, 6b and 6c are disposed to protrude outside the pressure-sensitive layer 4 is about three times higher than that of Comparative embodiment 1 where the whole area of the electrodes faces the pressure-sensitive layer, and therefore Embodiment 1 can prevent the electrical signals from attenuating due to the effect of the pressure-sensitive layer.

In addition, it is found that, with Comparative embodiment 1, the electrical signals when the pressed position P2 is pressed are attenuated by about six out of ten of those when the pressed position P1 is pressed, while with Embodiment 1, the electrical signals when the pressed position P2 is pressed are attenuated by about five out of ten of those when the pressed position P1 is pressed, and therefore Embodiment 1 can more surely prevent the attenuation of the electrical signals when the pressed position P2 far from the connection point to the oscilloscope is pressed. Furthermore, it is found that Embodiment 1 can more prevent the attenuation of the electrical signals at 5 Hz to 10 Hz than Comparative embodiment 1, and therefore can prevent the attenuation of the electrical signals at relatively high frequencies.

REFERENCE SIGNS LIST 1 piezoelectric sensor
2 analysis unit
3a, 3b, 31a, 31b electrode
4, 21 pressure-sensitive layer
5a, 5b terminal
6a to 6d edge
41a to 41c, 51a to 51f detecting part
42, 52 slit
P1, P2 pressed position
L bed
S living body

The invention claimed is:

1. A piezoelectric sensor configured to detect a change of pressure from a living body in a predetermined location, the piezoelectric sensor comprising:
 a pair of electrodes spaced from one another, each electrode formed as a sheet having an elongated shape;
 a pressure-sensitive layer disposed between the pair of electrodes and configured to generate electric charge in response to the change of pressure;
 a pair of terminals connected to the pair of electrodes, respectively, and configured to output an electrical signal supplied from the pair of electrodes in response to the change of pressure of the living body, wherein each electrode includes a longitudinally-extending edge, and each terminal of the pair of terminals is connected to a respective edge extending in the longitudinal direction,
 wherein one of the longitudinally-extending edges of at least one of electrodes protrudes outside the pressure-sensitive layer in a first direction, and one of the longitudinally-extending edges of another of the electrodes protrudes outside the pressure-sensitive layer in a second direction opposite the first direction so that the longitudinally extending edges of the pair of electrodes do not overlap with each other in a pressure-sensing direction, and
 wherein the electrical signal propagates through the first edges and is outputted from the pair of terminals.

2. A biological information analyzer comprising:
 the piezoelectric sensor according to claim 1, and
 an analysis unit configured to analyze biological information of the living body, based on electrical signals outputted from the pair of terminals.

3. The piezoelectric sensor, configured to detect a change of pressure from a living body in a predetermined location, the piezoelectric sensor comprising:
 a pair of electrodes spaced from one another and formed to spread as a sheet;
 a pressure-sensitive layer disposed between the pair of electrodes and configured to generate electric charge in response to the change of pressure;
 a pair of terminals connected to the pair of electrodes, respectively, and configured to output an electrical signal supplied from the pair of electrodes in response to the change of pressure of the living body,
 wherein an edge of at least one of the pair of electrodes extending toward the pair of terminals is disposed to protrude outside the pressure-sensitive layer, and the electrical signal propagates through the edge and is outputted from the pair of terminals, wherein:
 each of the pair of electrodes has a long rectangular shape; and
 at least one of the pair of electrodes includes a plurality of detecting parts divided from each other by slits which extends over a part overlapping the pressure-sensitive layer in a direction crossing a longitudinal direction.

4. The piezoelectric sensor according to claim 3, wherein the plurality of
 detecting parts are further divided by a silt extending in the longitudinal direction.

* * * * *